United States Patent [19]

Honma

[11] 3,945,799
[45] Mar. 23, 1976

[54] METHOD FOR QUANTITATIVELY DETERMINING OXYGEN CONTENT ORGANIC COMPOUNDS
[75] Inventor: Haruo Honma, Tokyo, Japan
[73] Assignee: Rikagaku Kenkyusho, Japan
[22] Filed: June 6, 1974
[21] Appl. No.: 477,030

[30] Foreign Application Priority Data
June 8, 1973  Japan............................ 48-64454

[52] U.S. Cl.......................... 23/230 PC; 23/253 PC
[51] Int. Cl.².......................................... G01N 31/12
[58] Field of Search................... 23/230 PC, 253 PC

[56] References Cited
UNITED STATES PATENTS
3,374,064  3/1968  Kolsto............................ 23/253 PC OTHER PUBLICATIONS
Walton et al. "Determination of Small Amounts of Oxygen in Org. Comp."; J. Res. Nat. Bureau of Standards, Vol. 40, 1948, pp. 443–447.

Kirsten "Recent Developments in Quantitative Org. Microanalysis"; Anal. Chem.; Vol. 25, No. 1, 1953, pp. 74–86.
Aluise et al. "Direct Determination of Oxygen in Oxy Comp.; Anal. Chem.; Vol. 23, No. 3 pp. 530–533.

Primary Examiner—Joseph Scovronek
Assistant Examiner—Arnold Turk

[57]         ABSTRACT

Disclosed is an improvement of quantitative analysis of oxygen content in an organic compound. The accuracy of the quantitative determination is substantially improved by adding hydrogen or methane to a carrier gas.

The carbon-reduction process is performed in the presence of hydrogen or methane in the thermal decomposition tube, thus retaining the catalyst in the state of not being contaminated with oxygen or oxygen compound by depriving the catalyst of the oxygen or oxygen compound which is released from the air and moisture undesirably entering the tube and from the thermal decomposition gas of the sample.

1 Claim, 3 Drawing Figures

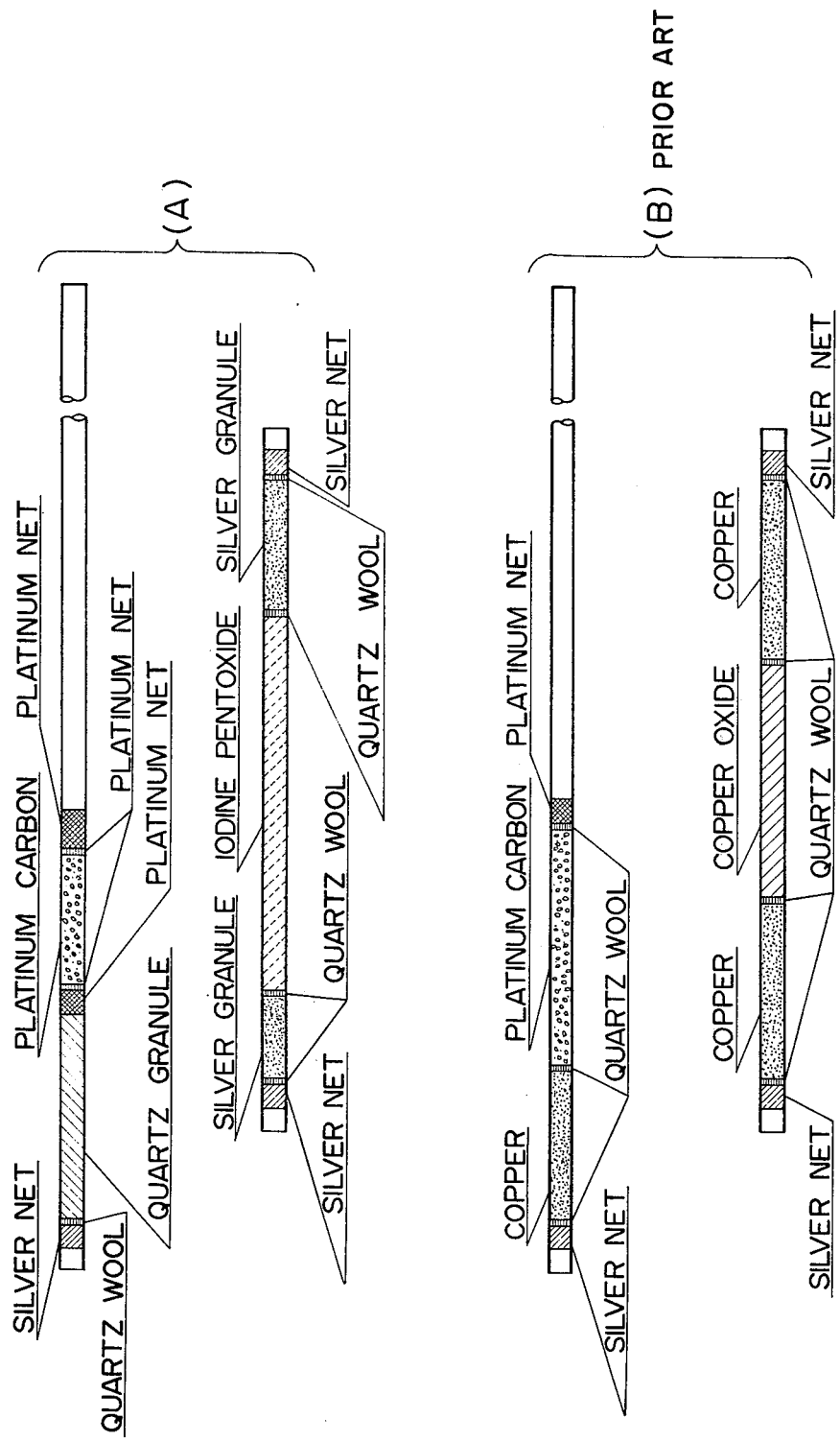

METHOD FOR QUANTITATIVELY DETERMINING OXYGEN CONTENT ORGANIC COMPOUNDS

This invention relates to an improvement in a method for quantitatively determining oxygen content in organic compounds by the carbon-reduction process and to a system for carrying out such method.

The art of quantitative analysis of oxygen in an organic compound generally belongs to a field of organic micro-quantitative analysis in analytic chemistry. The organic compound includes such principal elements as carbon, hydrogen, nitrogen and oxygen, and it is required that the organic micro-quantitative analysis accurately determine the composition ratio of these different elements within an allowance of absolute error of 0.3%. This microanalysis is indispensable for research in organic chemistry and related fields, such as determination of molecular structure, determination of molecular formula, identification of material or the like, and, in fact, it may be the only method for quantitative determination. Different quantitative analyses of oxygen have been proposed since H. ter Meulen and A. Götz et al. reported the hydrogen-reduction process in which analysis of oxygen is performed in a 100% hydrogen gas stream. However, the quantitative analysis for oxygen content in organic compounds which is predominantly employed at present is the carbonreduction process.

The oxygen quantitative analysis according to the carbon-reduction process uses nitrogen, argon, helium and other pure inert gases as a carrier, and comprises the steps of: thermally decomposing a sample of organic compound, introducing the resultant thermal-decomposition gas, which is entrained in the carrier gas, to a platinum-carbon or carbon catalyst (hereinafter referred to as "carbon-reduction catalyst") at an elevated temperature ranging from 900° to 1200°C, reduce all of oxygen compounds into carbon monoxide; oxidizing said carbon monoxide with copper oxide or iodine pentoxide to produce carbon dioxide or iodine; quantitatively determining the carbon dioxide or iodine thus produced by means of gravimetric process, volumetric process, differential thermal conduction process or the like; and finally determining the oxygen content in the organic compound from the result of quantitative determination of carbon dioxide or iodine.

The conventional method of quantitatively determining oxygen content according to the carbon-reduction process as described above, has many disadvantages which make it impracticable. These disadvantages can be enumerated as follows:

1. The conventional quantitative analysis of oxygen is less accurate than the quantitative analysis of carbon, hydrogen or nitrogen. In practice, it is difficult to maintain the absolute error below 0.3%.

2. It has a poor reproducibility. The same result cannot be assured, no matter how carefully the quantitative analysis is repeated on the same sample.

3. Different errors are caused by replacement of carbon-reduction catalysts and, oxidizing agents, and by recharging filling materials.

4. It has an increased "after-blank value". Even if preliminary tube heating has been effected for a long time, the "after-blank value" cannot be reduced, and the figure does not remain at a constant and is uncontrollable.

5. The "after-blank value" greatly varies with hours and days, and can be hardly maintained at a constant.

6. The "after-blank value" is different from the "ghost blank value" which is determined after the organic compound is thermally decomposed, and the "ghost blank value" is very large. Accordingly, even an organic compound containing no oxygen, when thermally decomposed, may exhibit blank value which would be found in thermally decomposing an organic compound having a 2 – 3% oxygen content.

It has been found that, among other factors, the most important cause for defects is the contamination of the carbon-reduction catalyst with oxygen or oxide compound during operation.

One source of the contamination is the air and moisture which enter a thermal decomposition tube when a sample is loaded in the tube, and the other is the oxygen compound (mainly, carbon monoxide) produced by the thermal decomposition of the sample and retained on the carbon-reduction catalyst. There would be no problem if the oxygen or oxygen compound were completely removed from the catalyst at the temperature ranging from 900° to 1000°C within the inactive gaseous atmosphere.

It appears that when the tube and the carbon-reduction catalyst are heated to the above temperature, as a preliminary step to measurement, the catalyst cannot be cleaned and that a part of the oxygen or oxygen compound is released from the carbon-reduction catalyst and is entrained in the carrier gas, and erroneously detectted as a part of the oxygen content of the sample.

Accordingly, the problems listed above can be solved by adding to the inactive carrier gas, hydrogen, methane or other reducing gases to remove from the carbon-reduction catalyst the oxygen compound which is adsorbed by or combined with the catalyst.

This invention is based on the discovery above mentioned.

The object of this invention is to provide a carbon-reduction type quantitative analysis of an organic compound in terms of oxygen content at as high precision (0.3% less absolute error) as in the quantitative analysis of carbon, hydrogen or nitrogen.

Another object of this invention is to provide a system for carrying out such quantitative analysis.

To attain these objects, quantitative analysis of oxygen according to this invention essentially comprises adding a proper amount of hydrogen or methane into a thermal decomposition tube at an intermediate stage of process to prevent the contamination of the carbon-reduction catalyst with oxygen or oxygen compound and to promote the separation of the carbon monoxide from the carbon-reduction catalyst.

This invention will be better understood from the following description which is made with reference to the accompanying drawings:

FIG. 3A illustrates the position of different filling materials in a thermal decomposition tube and an oxidizing tube used in the system according to this invention, and FIG. 3B shows a similar positioning employed in the conventional one.

FIG. 1 illustrates a system for carrying out the quantitative analysis of oxygen according to this invention, while FIG. 2 illustrates a conventional system for the comparative purpose.

Figure 1:
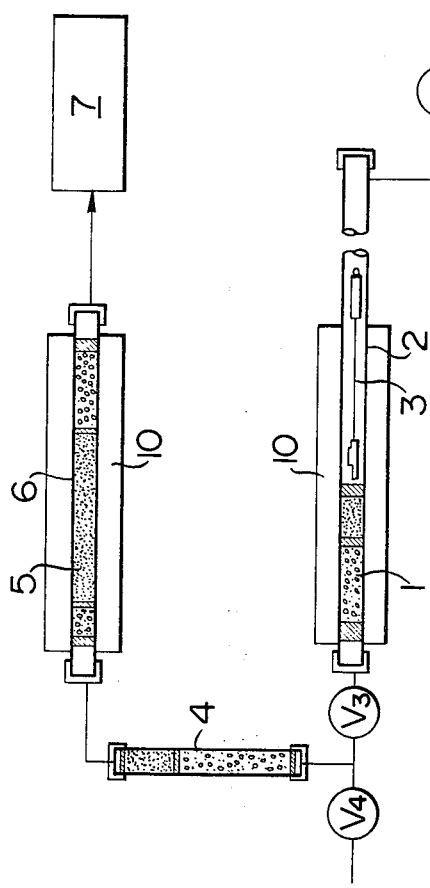
FIG. 1 is a block diagram illustrating an embodiment of the system for quantitatively analyzing the oxygen content of an organic compound according to this invention.
Figure 2:
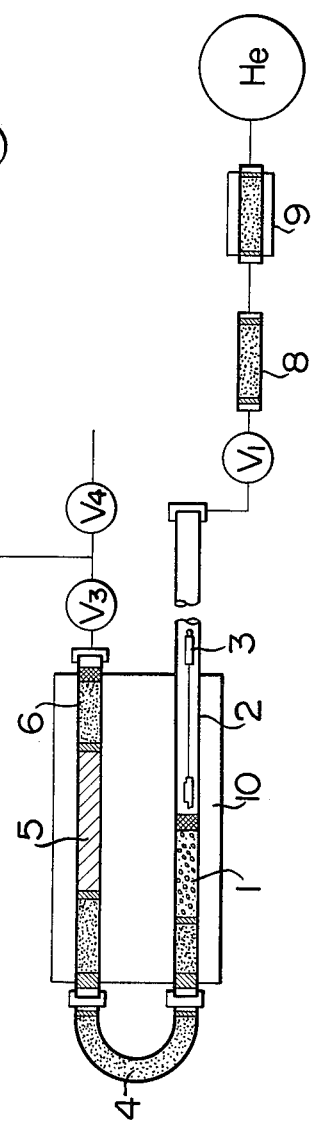
FIG. 2 is a similar block diagram but showing the conventional system.

In FIG. 1, a thermal decomposition tube 2 contains a carbon-reduction catalyst 1. A sample charging member 3 which carries a sample of organic compound is inserted in a thermal decomposition tube 2 from one end thereof.

(The sample is shown in this figure as positioned within the heating furnace 10, but this sample is at the right hand of the tube before the thermal decomposition is performed.) When the sample is inserted in the thermal decomposition tube 2, air and moisture enters the tube 2. By opening a valve $V_1$ and opening valves $V_3$ and $V_4$ helium is introduced to discharge the air and the moisture into atmosphere. After a few minutes the valves $V_1$, $V_3$ and $V_4$ are closed and a valve $V_2$ is opened so that a gas mixture of helium and hydrogen is fed into the thermal decomposition tube 2. Then, the valves $V_3$ and $V_4$ are opened so that the gas mixture is discharged into atmosphere. This purging continues for a few minutes, so that the carbon-reduction catalyst which has been contaminated with the oxygen content of the air and moisture is purified by the reducing action of hydrogen or methane. Then, the valves $V_4$, $V_3$ and $V_2$ are closed to cease the gas flowing. Then the sample is subjected to thermal decomposition under static state. At this stage of the process the thermal decomposition tube is filled with helium and hydrogen or methane. The hydrogen or methane assists to separate from the carbon-reduction catalyst, the oxygen compound produced by thermal decomposition of the sample and the carbon monoxide produced by reduction of the oxygen compound by the catalyst. After a few minutes the valves $V_3$ and $V_1$ are opened so that monoxides and the other thermal decomposition products are introduced into an acidic gas absorbing tube 4, which purifies the thermal decomposition products, and, after purification, they are fed into an oxidizing tube 6 which is filled with oxidizing agents, such as copper oxide or iodine pentoxide. When the copper oxide is used, the carbon monoxide is oxidized into carbon dioxide, while when the iodine pentoxide is used, the carbon monoxide is changed into carbon dioxide and iodine, and then the carbon dioxide or the iodine is measured by a quantitative analyzing system 7 to determine the oxygen content in the sample.

As will be understood from the above, in the method for quantitatively determining oxygen according to this invention, hydrogen or methane is introduced in the thermal decomposition tube at each measuring procedure, and the thermal decomposition is effected under static condition in the presence of the inactive gas and hydrogen or methane. Accordingly, the carbon-reduction catalyst is purified by reduction by means of hydrogen or methane, and thus the catalyst can be maintained in the same state without being contaminated with oxygen and oxygen compounds.

Example

The oxygen analysis was made on various standard samples, using the quantitative analyzing system according to the differential thermal conduction process, under the conditions given in Table 1. FIG. 3 shows the filling agents in the thermal decomposition tube and the oxidizing tube. FIG. 3A shows those tubes used in the system according to this invention and FIG. 3B shows those which are most widely used at present.

Table 1

| | Thermal decomposition tube | Oxidizing tube | Kinds of reaction gas added | Types of thermal decomposition system |
|---|---|---|---|---|
| Present Invention | Temp. of tube: 960°C. Platinum-carbon (50 mm), Platinum net, Granulated quartz | Temp. of tube: 220 – 240°C. Oxidizing agent: Iodine pentoxide | Hydrogen added (11–12 ml) | Static |
| Prior art | Temp. of tube: 960°C. Platinum-carbon (102 mm) Platinum net. Granulated copper | Temp. of tube: 650°C. Oxidizing agent: Copper oxide | No gas added | Dynamic |

Table 2 shows the sensitivities Ko, in determining the oxygen contents of the standard samples, and Table 3 shows the oxygen content values of these samples. As is apparent from these tables, the figures show the stability of sensitivity, compared with the sensitivity of the conventional system, and that oxygen content can be determined with a 0.3% or less absolute error.

Table 2

| Sample | Theoretic oxygen content (%) | Prior art Ko:μv/μgΔKo | Present invention Ko:μv/μgΔKo | Remarks |
|---|---|---|---|---|
| Succinic acid | 54.19 | 14.06    −0.42 | 12.91    +0.01) | |

Table 2-continued

| Sample | Theoretic oxygen content (%) | Prior art Ko:μv/μg | ΔKo | Present invention Ko:μv/μg | ΔKo | Remarks |
|---|---|---|---|---|---|---|
| Saccharose | 51.41 | 14.09 | −0.39 | 12.79 | −0.11 | Quantitative analysis was repeated five times on the same sample, and average value of the five measurements is given |
| m-dinitrobenzene | 38.07 | 14.32 | −0.16 | 12.81 | −0.09 | |
| Benzoic acid | 26.20 | 14.25 | −0.23 | 12.99 | +0.09 | |
| p-nitroaniline | 23.17 | 14.40 | −0.08 | 12.91 | +0.01 | |
| Acetoanilide | 11.87 | 14.78 | +0.30 | 12.88 | −0.02 | |
| Cholesterol | 4.14 | 15.45 | +0.97 | 12.99 | +0.09 | |
| Anthracene | 0 | 320μv | | −10μv | | Signal output |
| x̄ (average value of Ko) | | 14.48 | | 12.90 | | |
| R (range) | | 1.39 | | 0.20 | | |

$$Ko = \frac{\mu v \text{ (signal value (micro volts) given by the quantitative analyzing system)} \times 100}{\mu g \text{ (weight of the sample (micro grams))} \times \text{theoretic oxygen content(\%)}}$$

Table 3

| No. | Sample | Theoretic oxygen content (%) | Prior Art Oxygen content measured | Absolute error | Present Invention Oxygen content measured | Absolute error |
|---|---|---|---|---|---|---|
| 1 | Succinic acid | 54.19 | 54.20 | +0.01 | 54.17 | −0.02 |
| 2 | '' | | 54.26 | +0.07 | 54.22 | +0.03 |
| 3 | Saccharose | 51.41 | 51.35 | −0.06 | 51.30 | −0.11 |
| 4 | '' | | 51.86 | +0.45 | 51.33 | −0.08 |
| 5 | m-dinitrobenzene | 38.07 | 38.88 | +0.81 | 37.92 | −0.15 |
| 6 | '' | | 38.94 | +0.87 | 38.08 | +0.01 |
| 7 | Benzoic acid | 26.20 | 26.56 | +0.36 | 26.40 | +0.20 |
| 8 | '' | | 26.57 | +0.37 | 26.36 | +0.16 |
| 9 | p-nitroaniline | 23.17 | 23.64 | +0.47 | 23.23 | +0.06 |
| 10 | '' | | 23.62 | +0.45 | 23.25 | +0.08 |
| 11 | Acetoanilide | 11.84 | 12.47 | +0.63 | 11.90 | +0.06 |
| 12 | '' | | 12.44 | +0.60 | 11.87 | +0.03 |
| 13 | Cholesterol | 4.14 | 4.55 | +0.41 | 4.14 | ±0 |
| 14 | '' | | 4.56 | +0.42 | 4.14 | ±0 |
| 15 | Anthracene | 0 | 250− | — | | |
| 16 | | 0 | 370 μv | | 0−13μv | — |
| | | | x̄ 0.43 Actual sensitivity of first run of succinic acid = μv/μg = 14.05 | | x̄ 0.07 Actual sensitivity of first run of succinic acid = μv/μg = 12.85 | |

Similar results were obtained when cupric oxide is used as the oxidizing agent at a temperature of 200°C.

As is understood from the above the accuracy of the quantitative determination is much improved by adding hydrogen or methane to a carrier gas according to this invention.

Furthermore, the amount of charge of the oxygen-reducing catalyst required for this invention is about half of that required for the prior art method. The catalyst is not likely to be covered by thermal carbon, so that the harmful effect due to carbon is reduced and the catalyst can be used continuous operation for long time.

The present invention serves to elevate the art of the quantitative analysis of oxygen in organic compounds to the same level as that of the quantitative analysis of carbon, hydrogen, nitrogen and the like, thus permitting the accurate quantitative analysis of all the principal elements of an organic compound.

What is claimed is:

1. In the carbon-reduction quantitative method of determining oxygen in which an organic compound is subjected to thermal decomposition and oxygen is measured as oxides of carbon, the improvement comprising thermally decomposing said compound over a platinum-carbon or carbon catalyst in a static volume of inert gas containing a small amount of hydrogen or methane.

* * * * *